United States Patent
Dick et al.

(10) Patent No.: US 10,039,634 B2
(45) Date of Patent: Aug. 7, 2018

(54) INTRAOCULAR LENS PROVIDED FOR IMPLANTATION INTO AN EYE AND DEVICE FOR CHANGING THE OPTICAL EFFECT OF AN IMPLANTED INTRAOCULAR LENS

(75) Inventors: Manfred Dick, Gefell (DE); Pascal Bernard, Nieul sur mer (FR); Martin Kühner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 727 days.

(21) Appl. No.: 13/702,040

(22) PCT Filed: May 23, 2011
(Under 37 CFR 1.47)

(86) PCT No.: PCT/EP2011/058371
§ 371 (c)(1),
(2), (4) Date: May 17, 2013

(87) PCT Pub. No.: WO2011/151215
PCT Pub. Date: Dec. 8, 2011

(65) Prior Publication Data
US 2013/0297017 A1   Nov. 7, 2013

(30) Foreign Application Priority Data

Jun. 4, 2010   (EP) ..................... 10165024

(51) Int. Cl.
*A61F 2/16*   (2006.01)

(52) U.S. Cl.
CPC .......... *A61F 2/1613* (2013.01); *A61F 2/1635* (2013.01); *A61F 2002/1681* (2013.01)

(58) Field of Classification Search
CPC .... A61F 2/1613; A61F 2/1618; A61F 2/1654; A61F 2/1648; A61F 2/1629; A61F 2250/0001; A61F 2002/1681–2002/169053; A61F 2250/001; A61F 2210/0061
USPC ................................................. 623/6.27, 6.22
See application file for complete search history.

(56) References Cited

U.S. PATENT DOCUMENTS

| 4,575,373 A | 3/1986 | Johnson |
| 4,668,446 A * | 5/1987 | Kaplan .................... C08J 7/12 264/1.7 |
| 5,288,293 A * | 2/1994 | O'Donnell, Jr. ...... A61F 2/1613 623/6.22 |

(Continued)

FOREIGN PATENT DOCUMENTS

| JP | 2004187891 A | 7/2004 |
| WO | WO 02/071976 A2 | 9/2002 |
| WO | WO2010125596 * | 11/2010 ............... A61F 2/16 |

*Primary Examiner* — David H Willse
*Assistant Examiner* — Tiffany Shipmon
(74) *Attorney, Agent, or Firm* — Patterson Thuente Pedersen, P.A.

(57) ABSTRACT

An intraocular lens provided for implantation into an eye, includes a lens body having a central region, haptics for holding the intraocular lens in place within the eye after implantation, and an activatable zone outside the central region. After implantation of the intraocular lens into the eye, the lens body is deformed in the central region and/or at least one of the position, the rotation or the tilt of the intraocular lens within the eye changes upon irradiating only the activatable zone with laser radiation.

17 Claims, 11 Drawing Sheets

(56) References Cited

U.S. PATENT DOCUMENTS

| | | | |
|---|---|---|---|
| 5,571,177 A * | 11/1996 | Deacon | A61F 2/1613 |
| | | | 623/6.47 |
| 6,623,477 B1 | 9/2003 | Elbrecht et al. | |
| 6,726,679 B1 | 4/2004 | Dick et al. | |
| 2002/0133228 A1 | 9/2002 | Sarver | |
| 2003/0135271 A1* | 7/2003 | Bandhauer | A61F 2/1629 |
| | | | 623/6.22 |
| 2003/0187504 A1* | 10/2003 | Weinschenk, III | A61F 2/1616 |
| | | | 623/6.22 |
| 2005/0165387 A1 | 7/2005 | Lubatschowski et al. | |
| 2005/0182489 A1 | 8/2005 | Peyman | |
| 2009/0036880 A1 | 2/2009 | Bischoff et al. | |
| 2010/0082017 A1* | 4/2010 | Zickler | A61F 9/00834 |
| | | | 606/4 |

\* cited by examiner

INTRAOCULAR LENS PROVIDED FOR IMPLANTATION INTO AN EYE AND DEVICE FOR CHANGING THE OPTICAL EFFECT OF AN IMPLANTED INTRAOCULAR LENS

PRIORITY CLAIM

The present application is a National Phase entry of PCT Application No. PCT/EP2011/058371, filed May 23, 2011, which claims priority from German Application Number 10165024.0, filed Jun. 4, 2010, the disclosures of which are hereby incorporated by reference herein in their entirety.

BACKGROUND

An intraocular lens (IOL) is a lens to be implanted into an eye, usually to replace the existing crystalline lens because it has been clouded over by a cataract, or as a form of refractive surgery to change the eyes optical power. Although the insertion of a intraocular lens for treatment of cataracts is the most commonly performed eye surgical procedure it is still difficult to predict the refractive outcome after surgery. For example, position changes of the lens due to healing processes within the capsular bag after implantation can lead to refractive deviations. Refractive deviations can also result form unexpected tilt of the IOL. Or the rotation of an intraocular lens relative to the cornea is too high due to the healing process at the capsular bag or the cornea. The last is especially critical for toric IOLs intended to compensate for initial and/or induced corneal astigmatism

SUMMARY OF THE INVENTION

It is therefore object of the invention to provide an intraocular lens whose optical effect can be changed after implantation without the trauma, or increased surgical risk, of a further intraocular lens exchange.

The object is solved by an intraocular lens provided for implantation into an eye, comprising a lens body having a central region, haptics for holding the intraocular lens in place within the eye after implantation, and an activatable zone outside the central region, wherein, after implantation of the intraocular lens into the eye, the lens body is deformed in the central region and/or at least one of the position, the rotation and the tilt (inclination) of the intraocular lens within the eye changes upon only irradiating the activatable zone with laser radiation.

Since it is possible to deform the lens body in the central region and/or to change at least one of the position, the rotation and the tilt of the intraocular lens within the eye upon only irradiating the activatable zone with laser radiation no further intraocular lens exchange is necessary to change the optical effect of the implanted intraocular lens.

Due to the inventive intraocular lens it is sufficient to only irradiate the activatable zone in order to change the optical effect of the implanted intraocular lens, so that there is no need of applying laser radiation to the central region which could lead to a degradation of the central region of the lens body, for example with respect of scattering the light. The central region is preferably the region through which the light is transmitted when viewing.

The deformation of the central region of the lens body can be such that the refractive power of the central region of the lens body is amended. The refractive power can be enhanced or reduced. In particular, the radius of curvature of a surface of the lens body in the central region can be amended.

Further, the change of position of intraocular lens within the eye can be a displacement in the axial direction of the intraocular lens. This leads to an amendment of the refraction power of the whole eye in which the intraocular lens is implanted. Of course, it is also possible, that the change of position is a displacement perpendicular to the optical axis of the implanted intraocular lens. Any other direction of displacement is also possible.

Further by asymmetrically irradiating the activable zones or irradiating fewer or more compartments of this zone the intraocular lens can change is inclination or tilt against the visual or optical axis. So unwanted tilts of the IOL severely detoriating vision can be corrected.

Further the rotation of the intraocular lens, especially toric intraocular lenses, relative to the cornea can be changed. So a deviation of the relative rotation from the intended state due to healing process of the capsular bag and/or the cornea after surgery or initial positional errors at surgery can be compensated.

The activatable zone of the intraocular lens can comprise an elastically deformed region which expands at least partly upon being irradiated with the laser radiation. The direction of expansion can be in the direction of the optical axis of the intraocular lens, perpendicular to the optical axis of the intraocular lens or in any other direction.

In particular, the elastically deformed region can be formed by a compressed hollow region. The compressed state of the hollow region can be maintained by using an adhesive.

The activatable zone can comprise an internal tension in the material of the lens body and/or of the haptics. Such an internal tension can be provided by an inhomogeneous density and/or a combination of different materials.

The haptics can comprise a folded structure, for example a bellow structure. In particular, the folded structure can be tensioned which can be loosened by laser radiation. Therefore the optically activatable zone need not be colocalized with the structure under stress.

Further, the activatable zone of the intraocular lens can comprise hydroscopic material which is encapsulated by a hydrophobic layer which can be perforated by the laser radiation. If the hydrophobic layer is perforated the hydroscopic material can swell due to the aqueous humour leading to a change of volume. This change of volume can be used for deforming the central region and/or for changing the position or tilt or rotation of the intraocular lens within the eye.

It is possible, that the activatable zone of the intraocular lens comprises a material having a hydroscopic property which can be enhanced by irradiating with the laser radiation. If the hydroscopic property is enhanced the material will swell leading to a change of volume. This change of volume can be used for deformation of the central region of the lens body and/or for a change of the position or tilt or rotation of the implanted intraocular lens.

It is possible, that the activatable zone of the intraocular lens comprises a material having a hydroscopic property and being crosslinked or entangled so that further swelling is impeded. If by irradiating with light these crosslinks or entanglements are reduced the material will swell leading to a change of volume. This change of volume can be used for deformation of the central region of the lens body and/or for a change of the position or tilt or rotation of the implanted intraocular lens.

The material of the IOL can consists of or can comprise silicone or acrylates like Polymethyl-methacrylate and/or hydrophilic derivatives like hydroxylmethacrylates or other hyrdogel materials.

The activatable zone has preferably a ring shape (in particular in case of deformation of the central region of the lens body). In particular, the activatable zone can comprise a plurality of rings. The activatable zone can have several sub-zones.

Further, the central region can have at least the size of the dark-adapted pupil of the eye into which it is implanted. In this case it can be surely avoided that the optical used region is detoriated when changing the optical effect of the implanted intraocular lens since the laser radiation is only applied outside the central region and therefore outside the optical used region of the implanted intraocular lens.

The central region can be a circular region, seen in plane view, having a diameter of at least 6 to 8 mm.

The activatable zone can be rotationally symmetrical. The activatable zone is preferably provided within the lens body. However, it is also possible that the haptics or the root of the haptic comprise the activatable zone. This is especially preferred in case of changing tilt or rotation or position of the central body of the IOL, without changing the shape of the IOL. Further preferred is an arrangement of several activatable zones, which supports movement of the haptic ends relative to the IOL central body in all 3 space dimensions. In addition, the activatable zone can be within the lens body and within the haptics.

There is further provided the device for changing the optical effect of the inventive intraocular lens being implanted in an eye (in particular within the capsular bag of an eye), said device comprising a laser device including a laser radiation source providing pulsed laser radiation and an optical unit applying said pulsed laser radiation to the implanted intraocular lens, and a control unit which controls the laser device such that the laser radiation is directed only in the activatable zone in order to deform the lens body in the central region and/or to change the position of the intraocular lens within the eye for changing the optical effect of the implanted intraocular lens.

With such a device it is possible to change the optical effect of the intraocular lens after implantation so that further intraocular lens exchange is not necessary in order to compensate for deviations caused for example due to surgery biomechanical changes and healing processes within the capsular bag.

The laser device and the control unit can be such that the pulsed laser radiation comprises a pulse width of less than 10 ps, for example less than 700 fs or about 300 fs, with a pulse energy of about 0.1-10 µJ (in particular 1 µJ) and a focus diameter of about 5 µm. The wavelength of the laser radiation can lie in the range of 400-1.300 nm, for example between 780 and 1.060 nm. The laser radiation can also be a continuous radiation.

The changing device can comprise a measuring unit for measuring the eye-sight defect of the eye with the implanted intraocular lens. The measuring unit can comprise a refractometer or an aberrometer. But 3D imaging devices like OCT- or Scheimpflug-devices can be used as well.

The measuring result of the measuring unit can be used to generate control data. The control data are transmitted to the control unit. When operating the changing device with said control data a deformation of the lens body and the central region and/or a position change of the implanted intraocular lens is carried out such that the measured eye-sight defect is reduced or preferably completely corrected.

Thus, the control data are generated such that using these control data for the changing device leads to the designed reduction or correction of the eye-sight defect. The control data are generate by a separate generation device. However, the generation device can be part of the measuring unit and/or of the control unit.

The effect of the laser radiation can be controlled such that due to thermal effects and/or non linear effects the desired result is achieved in the activatable zone. Further, it is possible, that the property of the material is amended (e.g. a polymer material in the activatable zone is cracked). In addition, the pulsed laser radiation can induce several processes which may take place within a time sequence. If the power density of the radiation is above a threshold value during any pulse, an optical breakdown may appear, which, for example, would form a plasma bubble in the activatable zone. The plasma bubble then grows, due to expanding gas after the optical breakdown has formed. If the optical breakdown is not maintained, the gas generated in the plasma bubble is absorbed by the surrounding material, and the bubble disappears. Material-separating effect, acting without plasma bubbles, are also possible.

There is provided a method for preparing control data for the device for changing the optical effect of the implanted intraocular lens, said method comprises the following steps:
 determining measurement data relating to the eye-sight defect of the eye into which the intraocular lens is implanted,
 defining a necessary deformation of the lens body in the central region and/or a necessary change of at least one of the position, the inclination and the rotation of the intraocular lens within the eye for correcting the eye-sight defect,
 generating control data for the control unit (taking into consideration the defined necessary deformation and/or at least one of the defined necessary position change, inclination change and rotation change), wherein operating the changing device with said control data will result in the deformation and/or position, inclination and/or rotation change according to the defining step.

The measurement data can be generated by measuring the eye with the implanted intraocular lens. The measurement can be carried out with a wavefront measurement device, a refractometer or an aberrometer for example. But 3D imaging devices like OCT- or Scheimpflug-devices can be used as well.

There is provided a method for changing the optical effect of an implanted intraocular lens, the intraocular lens comprising a lens body having a central region, haptics for holding the intraocular lens in place within the eye after implantation, and an activatable zone outside the central region, that method comprising the following step:
 only irradiating the activatable zone with laser radiation such that the lens body is deformed in the central region and/or at least one of the position, the inclination and the rotation of the intraocular lens within the eye is changed in order to change the optical effect of the implanted intraocular lens.

With this method it is possible to change the optical effect of the implanted intraocular lens in order to compensate for deviations due to healing processes within the capsular bag after implantation, for example.

The method can comprise the step of dilating the iris of the eye before the irradiating step.

The method can comprise the step of expanding an elastically deformed region of the activatable zone by irradiating with the laser radiation.

Further, in the method, the laser radiation can be used to perforate a hydrophobic layer encapsulating hydroscopic material within the activatable zone.

The laser radiation can be used to enhance a hydroscopic property of material within the activatable zone (for example by cracking polymers).

In the method pulsed laser radiation can be used.

Further, the method can comprise a measuring step in order to determine the change of the optical effect of the implanted intraocular lens needed for reducing an eye-sight defect. After the measuring step the step of irradiating the activatable zone can be carried out in order to achieve the needed change.

The deformation of the lens body results for example in an amended radius of curvature of a surface of the lens body in the central region. The change of position of the intraocular lens within the eye (preferably within the capsular bag) is along the optical axis of the intraocular lens or perpendicular thereto. The inclination of the intraocular lens relative to the optical or visual axis or the orientation of the intraocular lens relative to the orientation of the cornea can be changed too. Further, any other direction of movement or inclination or rotation is possible.

The above described method for preparing control data may be further embodied such that further embodiments of the inventive method of changing the optical effect of an implanted intraocular lens can be carried out.

The above-mentioned method of changing the optical effect of an implanted intraocular lens can be combined with steps for implanting the intraocular lens. In particular, there is provided a method for implanting an intraocular lens comprising the steps:

implanting an intraocular lens within an eye (for example within the capsular bag of the eye), the intraocular lens comprising a lens body having a central region, haptics for holding the intraocular lens in place within the eye after implantation, and an activatable zone outside the central region measuring the eye-sight defect of the eye with the implanted intraocular lens, applying laser radiation only to the activatable zone leading to a deformation of the lens body in the central region and/or to a change of at least one of position, inclination (tilt) and rotation of the intraocular lens within the eye in order to compensate for the measured eye-sight defect.

It will be appreciated that the features mentioned above and those yet to be explained below can be used not only in the indicated combinations, but also in other combinations or alone, without departing from the scope of the present invention.

BRIEF DESCRIPTION OF THE DRAWINGS

The invention will be explained below in closer detail by reference to the enclosed drawings which also disclose features relevant to the invention, wherein.

DETAILED DESCRIPTION

Figure 1:
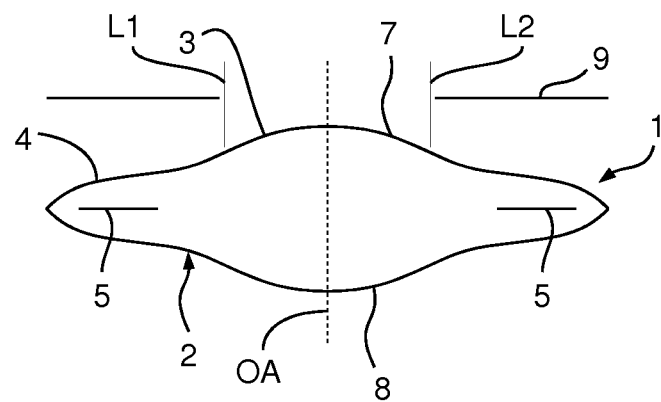
FIG. 1 depicts a schematic sectional view of an implanted intraocular lens.

FIG. 1 is a schematically sectional view of an intraocular lens 1 according to a first embodiment of the invention. The intraocular lens 1 is implanted in a capsular bag of a human eye. In FIG. 1 only the iris 9 of the eye is schematically shown.

The intraocular lens 1 comprises a lens body 2 having a central region 3 and an outer region 4 surrounding the central region 3.

The size of the central region 3 (as indicated by lines L1 and L2) is preferably selected such that only the central region 3 is used for viewing after implantation. In particular, the central region 3 has at least the size of the dark-adapted pupil of the eye into which the intraocular lens 1 is implanted. The central region 3 can be a circular region, seen in top view, having a diameter of about 6-8 mm.

The lens body 2 comprises an activatable zone 5 in the outer region 4. The activatable zone 5 has a ring shape and is elastically deformed.

Figure 2:
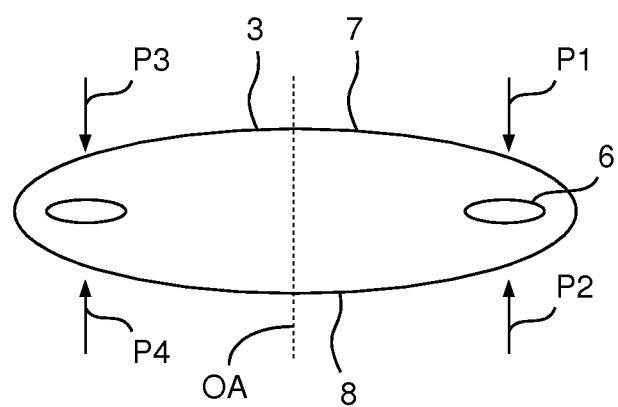
FIG. 2 depicts the intraocular lens before implantation.

This can be realized by providing an annular hollow space 6 in the outer region 4 of the lens body 2 as shown in FIG. 2. FIG. 2 shows a step for generating the intraocular lens 1 to be implanted.

There is provided an adhesive within the annular hollow space 6 and the annular hollow space 6 is pressed together as indicated by arrows P1-P4. The adhesive within the annular hollow space 6 fixes the compressed hollow space 6 so that the elastically deformed outer region 4 is maintained even if the forces for compressing the hollow space 6 are no longer applied.

Due to the elastically deformed outer region 4 the radius of curvature of the first and second surface 7, 8 of the lens body 2 in the central region 3 is smaller compared with the corresponding radius of curvature without the elastically deformed region 4 as shown in FIG. 2. Therefore, the refractive power of the intraocular lens 1 is enhanced by providing the elastically deformed region 5.

If the intraocular lens 1 is used for a cataract surgery there exists the difficulty of predictability of the refractive outcome after surgery. Also with the best diagnosis/measurement before, and implantation of the intraocular lens 1 having the best predetermined lens power, during a surgery biomechanical changes as well as position changes of the intraocular lens due to healing processes within the capsular bag can occur, which lead to refractive deviations. By using the intraocular lens 1 according to the invention and the following steps deviations can be corrected without the trauma, or increased surgical risk, of a further intraocular lens exchange or surgical corrective procedure.

Figure 3:
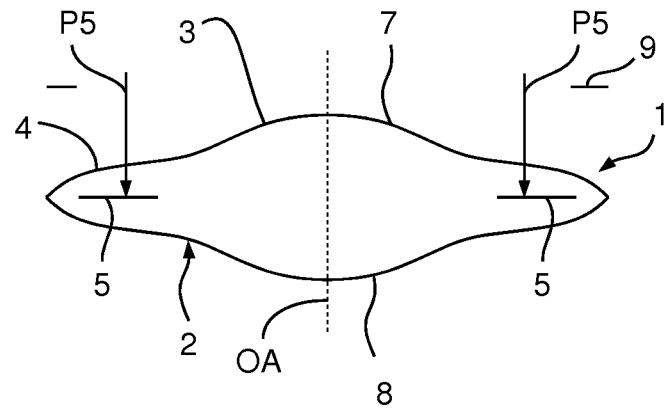
FIG. 3 depicts the implanted intraocular lens while being irradiated with laser radiation.
Figure 4:
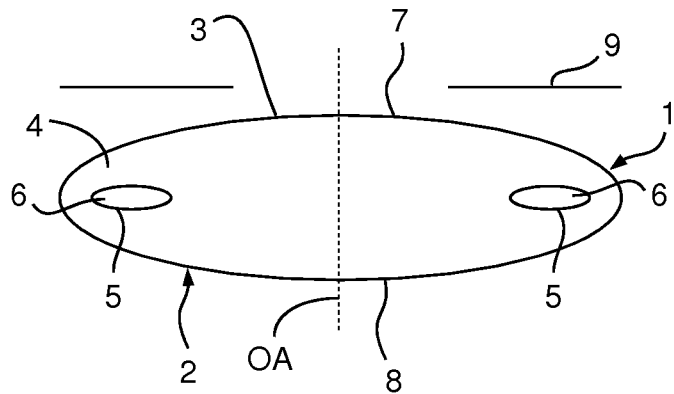
FIG. 4 depicts shows the implanted intraocular lens after laser irradiation.

As shown in FIG. 3, the iris 9 is dilated by using known drugs so that the outer region 4 of the lens body 2 can be irradiated with laser radiation P5. The laser radiation P5 is used to carry out a cut within the activatable zone 5 so that the adhesive does no longer fix the compressed annular hollow space 6. This leads to an expansion of the elastically deformed region 5 so that the radius of curvature of the first and second surfaces 7, 8 of the lens body 2 in the central region 3 is increased leading to a reduced refractive power (FIG. 4).

Figure 5:
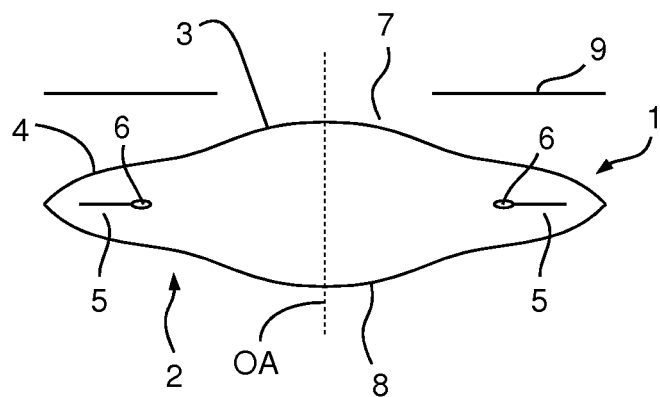
FIG. 5 depicts the implanted intraocular lens after another kind of laser irradiation.

The laser radiation can be controlled such that only a part of the activatable zone 5 is expanded (as shown in FIG. 5) so that the amount of amendment of refractive power can be exactly controlled. The step of dilating the iris 9 is not shown in FIG. 5 and will not be shown in the figures of the further embodiments. However, if necessary, the dilating step is carried out before applying the laser radiation.

Figure 6:
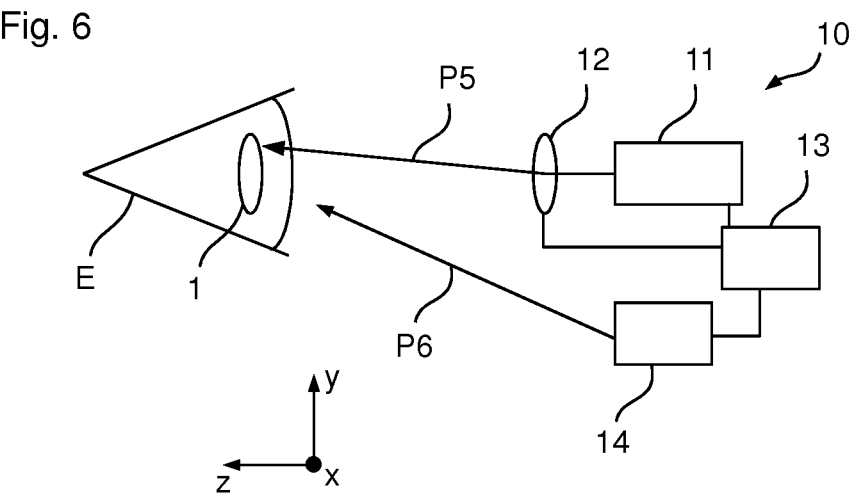
FIG. 6 depicts schematically a device for changing the optical effect of an implanted intraocular lens.

FIG. 6 shows a device 10 for changing the optical effect of the intraocular lens 1 implanted into the eye. The device 10 comprises a laser radiation source 11, an optical unit 12, a control unit 13, and a measuring unit 14. The control unit 13 controls the operation of the laser radiation source 11, the optical unit 12 and of the measuring unit 14.

The laser radiation source 11 is a Yb-fiber laser which emits laser pulses having a wavelength of about 1030 nm and a pulse duration of 300 fs. The pulse energy lies in the range of 0.1-10 µJ.

The optical unit 12 is used to focus the laser radiation in the activatable zone 5. The focus diameter is about 5 µm. Further, the optical unit 12 can deflect the laser radiation in at least two spatial directions. In particular, the optical unit 12 can shift the focused laser spot in three spatial directions. For shifting the first spatial direction (usually the z-direction), the optical unit 12 may for example comprise a zoom lens which is provided as an adjustable telescope, and for the other two spatial directions (usually the x- and the y-direction; the x-direction is perpendicular to the z- and y-direction), it may comprise to oscillating mirrors with crossed axes of rotation. Therefore, the laser spot can be moved within the lens body 2 in order to carry out the desired cut.

It is not necessary that a cut is carried out. It is also possible to loosen the adhesive effect of the adhesive with the thermal energy of the laser radiation leading to the desired expansion of the activatable zone 5 for altering the optical power of the central region 3 of the lens body 2.

The measuring unit 14 can be used to measure the eye-sight defect after implantation of the intraocular lens 1 (as indicated by arrow P6). The measurement results are transmitted to the control unit 13 which uses the measurement results to control the laser radiation source 11 and the optical unit 12 such that the resulting deformation of the central region 3 of the lens body 2 after laser irradiation of the activatable zone 5 corrects the measured eye-sight defect.

Figure 7:
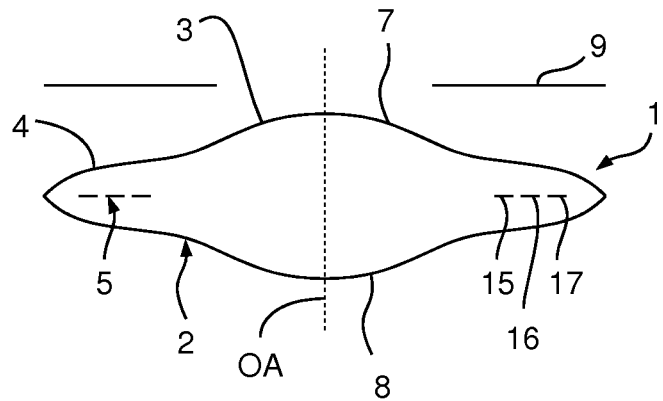
FIG. 7 depicts a further embodiment of an implanted intraocular lens.
Figure 8:
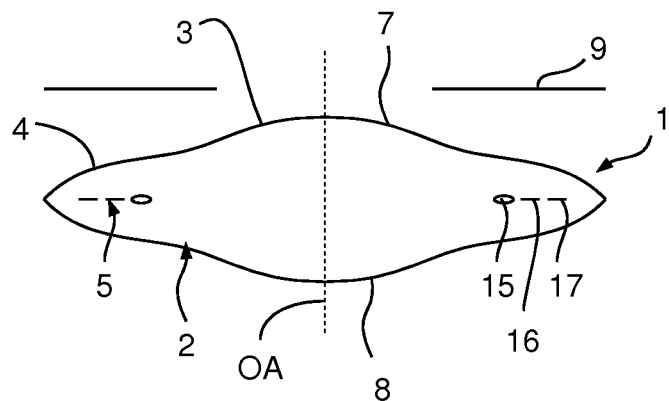
FIG. 8 depicts the implanted intraocular lens of FIG. 7 after laser irradiation.

A further embodiment of the intraocular lens 1 is shown in FIG. 7. In this embodiment, the activatable zone 12 is divided in three subzones 15, 16, 17. Each subzone 15-17 is a compressed annular hollow space fixed by an adhesive. By expanding only the first subzone 15 using the laser radiation of the laser radiation source 11 the amendment of the refractive power of the central region 3 of the lens body 2 (FIG. 8) is smaller than the amendment of the embodiment shown in FIG. 4.

Therefore, by selectively expanding at least one of the subzones 15-17 the amount of amendment of refractive power of the implanted intraocular lens 1 can be set in small steps. It is of course possible to only provide two subzones or to provide more than three subzones 15-17.

Figure 9:
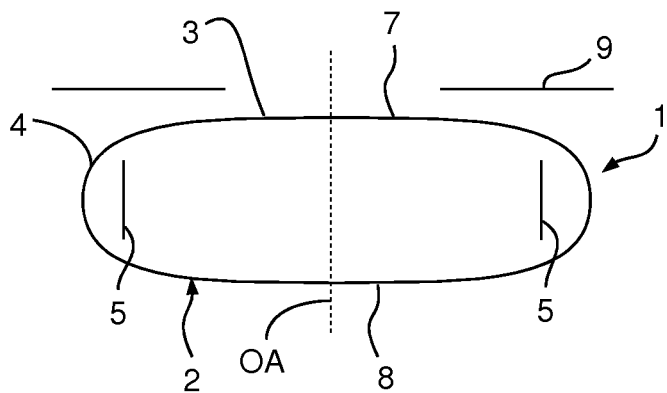
FIG. 9 depicts another embodiment of an implanted intraocular lens.
Figure 10:
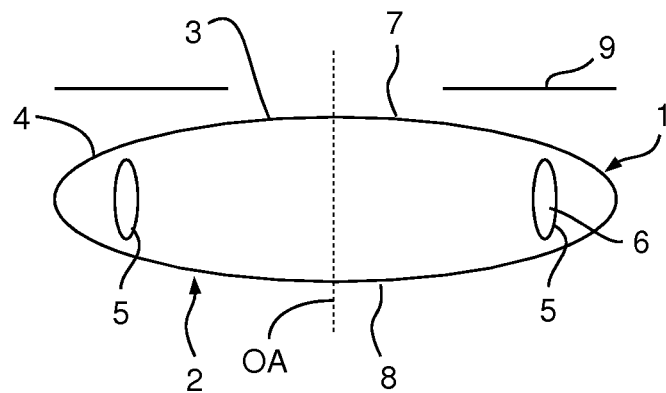
FIG. 10 depicts the implanted intraocular lens of FIG. 9 after laser irradiation.

In the above described embodiments the expansion of the activatable zone 5 leads to a reduction of the refractive power of the implanted intraocular lens 1. FIG. 9 shows an embodiment of the intraocular lens 1 being designed for increasing the refractive power after implantation. In this embodiment the activatable zone 5 comprises a compressed hollow space fixed by an adhesive which is compressed in a direction perpendicular to the optical axis OA of the lens body 2. If the adhesive is loosened the activatable zone will expand leading to an increased optical power of lens body 2 in the central region 3 as shown in FIG. 10.

It is of course possible to combine the embodiment of FIG. 9 with one of the previous embodiments so that the refractive power of the implanted intraocular lens 1 can be increased or decreased depending on the eye-sight defect after implantation.

Figure 11:
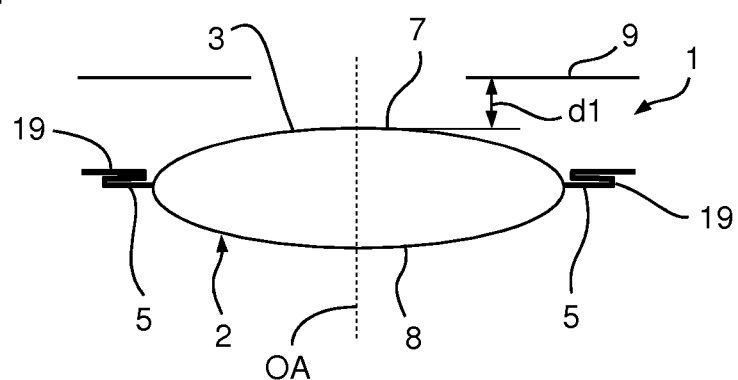
FIG. 11 depicts a further embodiment of an implanted intraocular lens.
Figure 12:
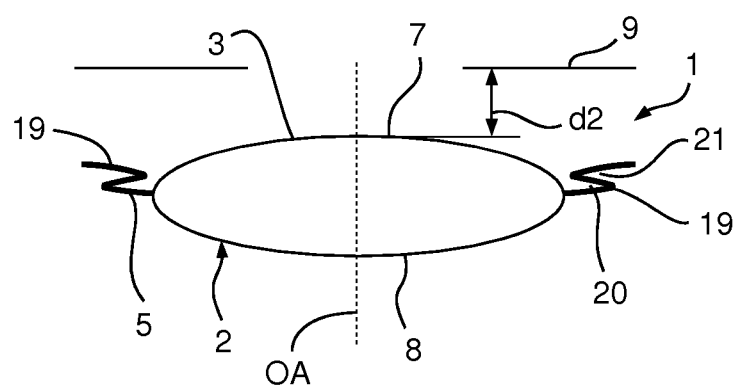
FIG. 12 depicts the implanted intraocular lens of FIG. 11 after laser radiation.

The intraocular lens 1 shown in FIG. 11 comprises haptics for fixing the position of the implanted intraocular lens 1 within the capsular bag. As can be seen in FIG. 11, the haptics have a folded form which is fixed by an adhesive. The adhesive effect can be loosened by laser radiation of the device 10 described above leading to an displacement of the lens body 2 of the intraocular lens 1 in the axial direction (FIG. 12). That means, that the distance d2 between the apex of the first surface 7 of the lens body 2 and the iris 9 is greater than the distance d1 (FIG. 11) without the expanded haptics 19 leading to a different refractive effect for the eye into which the intraocular lens 1 is implanted.

In FIG. 12 both adhesive portions 20, 21 are loosened. However, it is possible, to loosen only one of the two portions 20, 21 leading to a reduced axial displacement. In this way, an exact adaption of the refractive effect of the intraocular lens 1 for the eye can be adjusted.

Of course the intraocular lenses 1 according to the previous embodiments can comprise the haptics 19.

Figure 13:
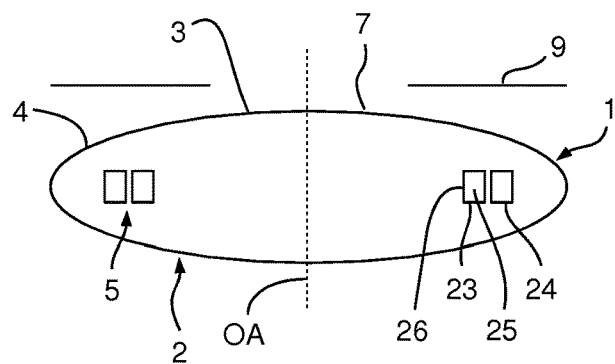
FIG. 13 depicts a further embodiment of an implanted intraocular lens.

A further embodiment of the intraocular lens 1 is shown in FIG. 13. In this embodiment the activatable zone 5 comprises two annular subzones 23, 24. In each subzone 23, 24 there is provided an hydroscopic material 25 which is encapsulated by a hydrophobic layer 26. The hydroscopic material 25 is provided in a first state being able to swell when coming into contact with aqueous humour. The swelling property is such that the swollen hydroscopic material 25 has a volume which is about 10 to 15% higher than the non-swollen hydroscopic material 25.

Figure 14:
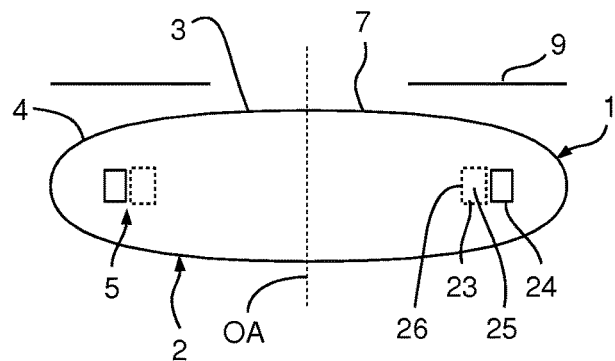
FIG. 14 depicts the intraocular lens of FIG. 13 after laser radiation.

In order to amend the refractive power of the central region 3 of the lens body 2 of the implanted intraocular lens 1 the hydrophobic layer 26 is perforated using the laser radiation so that the hydroscopic material 25 comes into contact with the aqueous humour. As a result the hydroscopic material 25 swells (as indicated in FIG. 14) leading to an amended radius of curvature of the first and second surfaces 7, 8 of the central region 3 of the lens body 2.

Since two subzones 23, 24 are provided, the amendment of the refractive power can be controlled in defined steps. Of course, it is possible to provide more than two subzones 23, 24.

Figure 15:
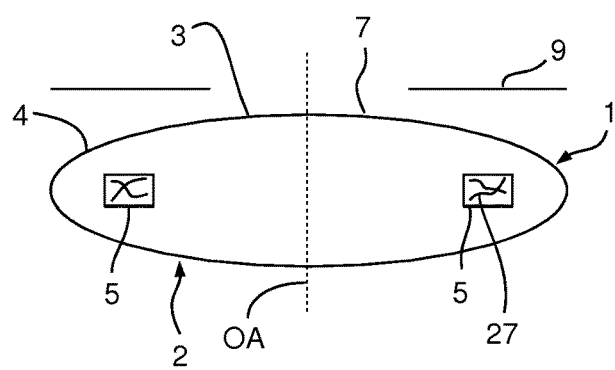
FIG. 15 depicts a further embodiment of an implanted intraocular lens.
Figure 16:
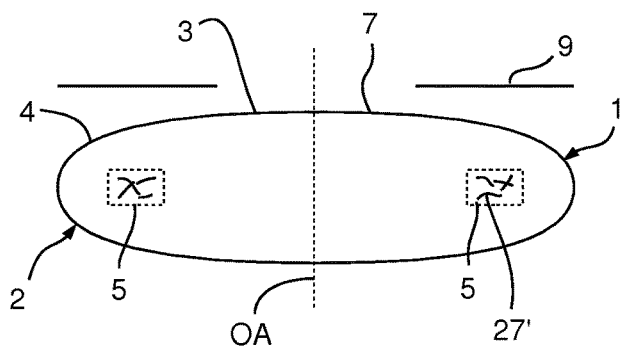
FIG. 16 depicts the intraocular lens of FIG. 15 after laser irradiation.

In the embodiment shown in FIG. 15 the activatable zone 5 comprises polymers 27. These polymers can be cracked by the laser radiation of the laser radiation source 11 leading to an enhanced hydroscopic effect or enhanced hydroscopic property or just reducing the elastic contracting forces of the crosslinked or entangled polymer network of the activatable zone 5. Therefore, the activatable zone 5 swells due to penetrating aqueous humour leading to a reduced refractive power of the central region 3 of the lens body 2 as shown in FIG. 16, wherein the cracked polymers are indicated with reference numeral 27'.

Figure 17:
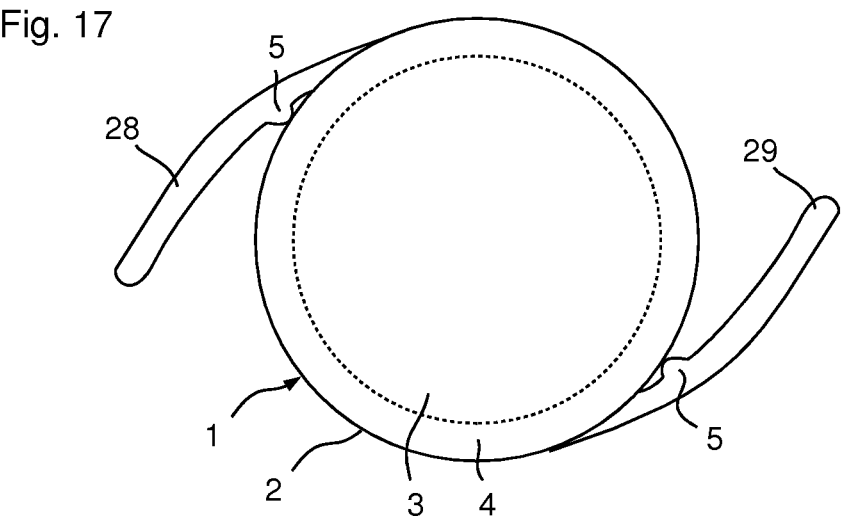
FIG. 17 depicts a further embodiment of an intraocular lens in plan view.
Figure 18:
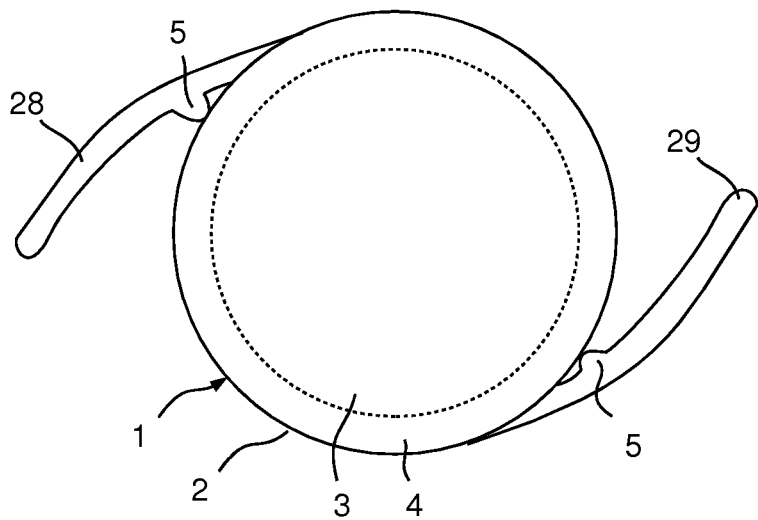
FIG. 18 depicts the intraocular lens of FIG. 17 after laser irradiation.

FIG. 17 shows an intraocular lens 1 according to a further embodiment in plan view. The intraocular lens comprises the lens body 2 and two side struts (haptics) 28, 29 having an activatable zone 5. The activatable zone 5 can be designed in the same way as one of the previous embodiments. After applying laser radiation to the activatable zone 5 of the first side strut 28 the first side strut 28 is swung out or moved away from the lens body 2. This can be used for adapting the haptics 28, 29 to the capsular bag dimension.

Figure 19:
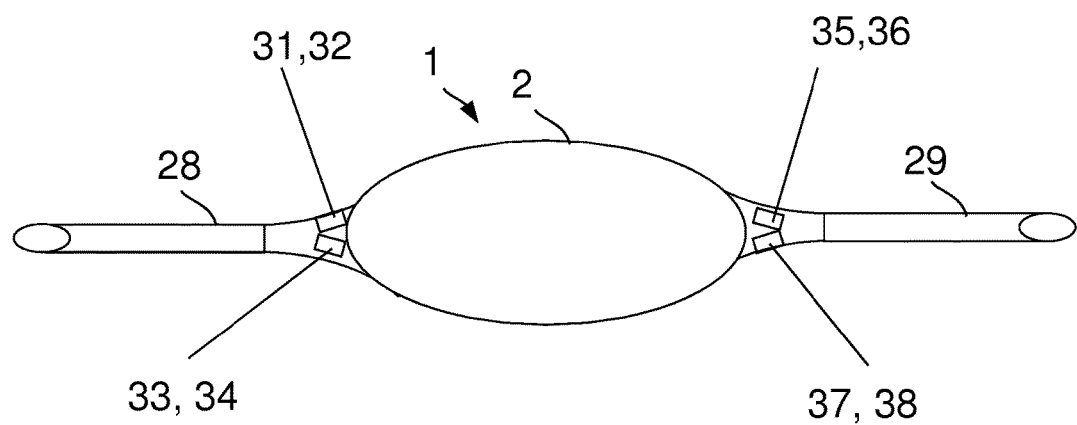
FIG. 19 depicts a further embodiment of an intraocular lens in cross section.
Figure 20:
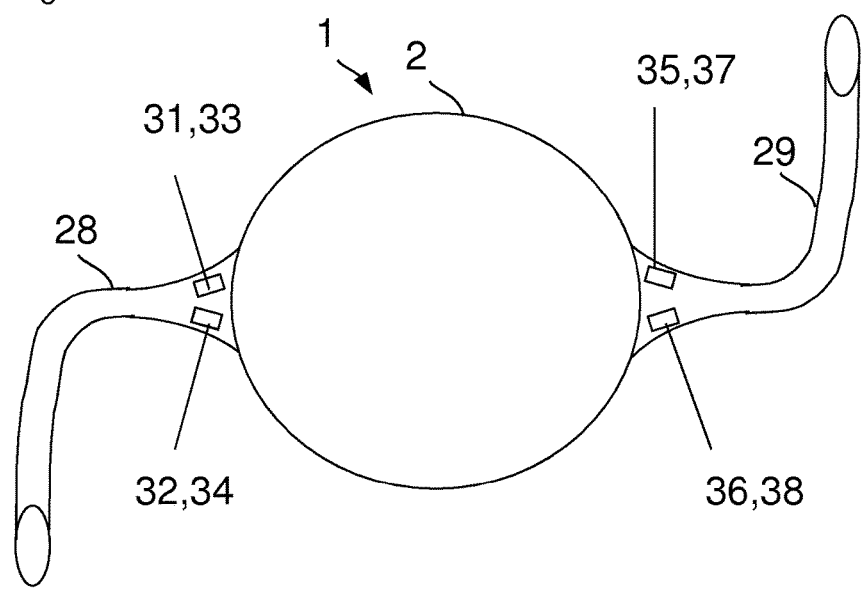
FIG. 20 depicts the intraocular lens of FIG. 19 in plan view.
Figure 21A:
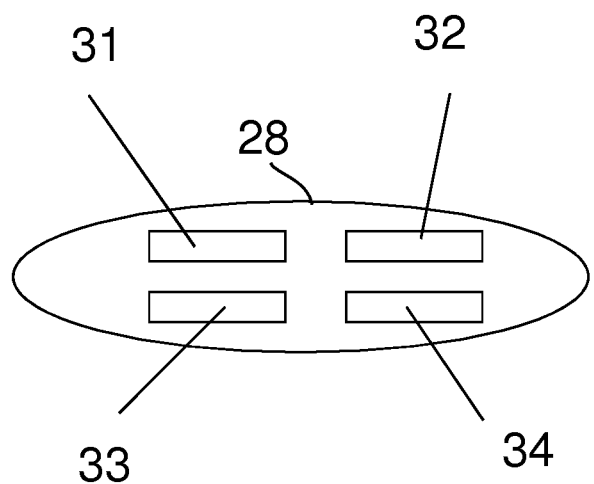
FIGS. 21a, b depict the arrangement of the activable zones in the intraocular lens of FIG. 19 as cross-section at the root of the haptics.
Figure 21B:
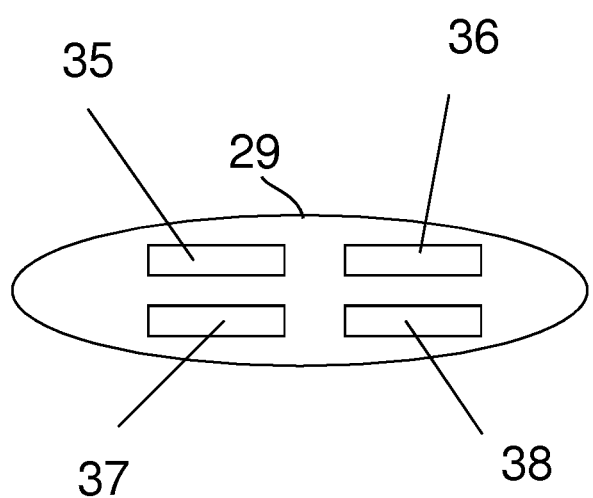

FIGS. 19 and 20 show a intraocular lens 1 according to a further embodiment in cross-sectional and plan view. In the root of the haptic 28, 29, where the haptic 28, 29 is connected to the main body 2 of the intraocular lens 1, there are several activatable zones 31, 32, 33, 34, 35, 36, 37, 38 arranged in a way as shown in FIGS. 21a and 21b. By activating of the appropriate zones 31-38 with laser/light irradiation the respective haptic 28, 29 is inclined or extended thus leading to a movement of the haptic end relative to the main body 2 of the intraocular lens 1. Since the haptic ends stay approximately fixed to the zonular region (or fixed within the capsular bag) the main body 2 of the intraocular lens 1 is repositioned within the capsular bag.

Figure 22A:
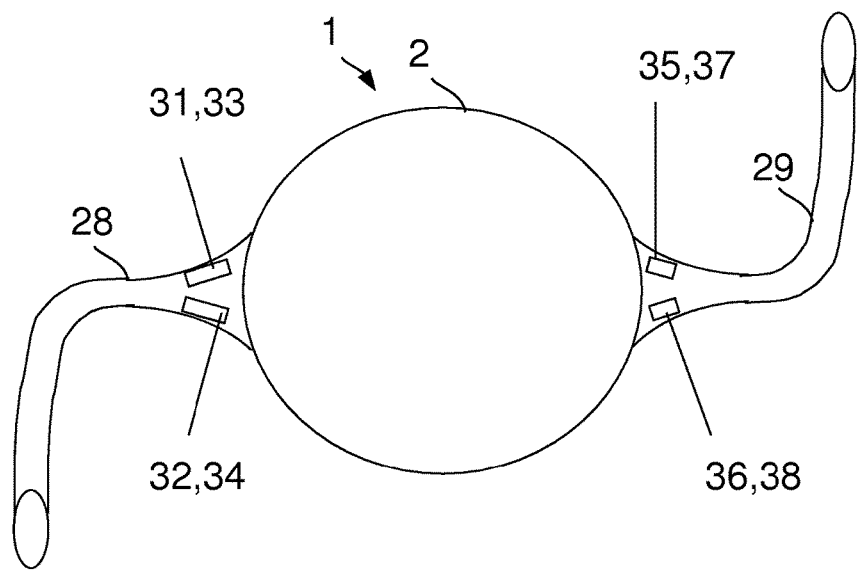
FIGS. 22a, b depict the intraocular lens of FIG. 19 after specific laser/light irradiation to cause shift of centration in one lateral direction of the IOL.
Figure 22B:
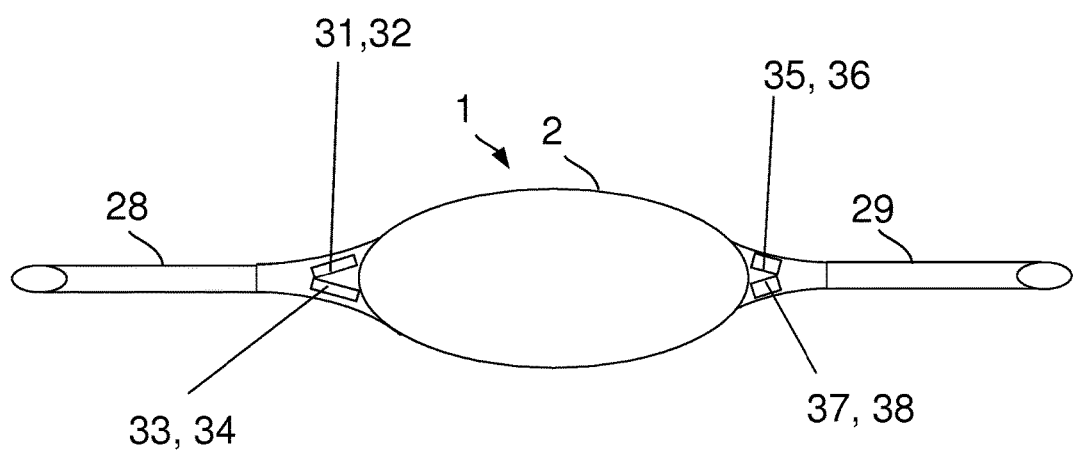

As shown by the plan view of FIG. 22a and by the sectional view of FIG. 22b, the main body 2 of the intraocular lens 1 is shifted to the right relative to the haptic end points by activating and thus extending zones 31, 32, 33, 34 to same extent.

Figure 23:
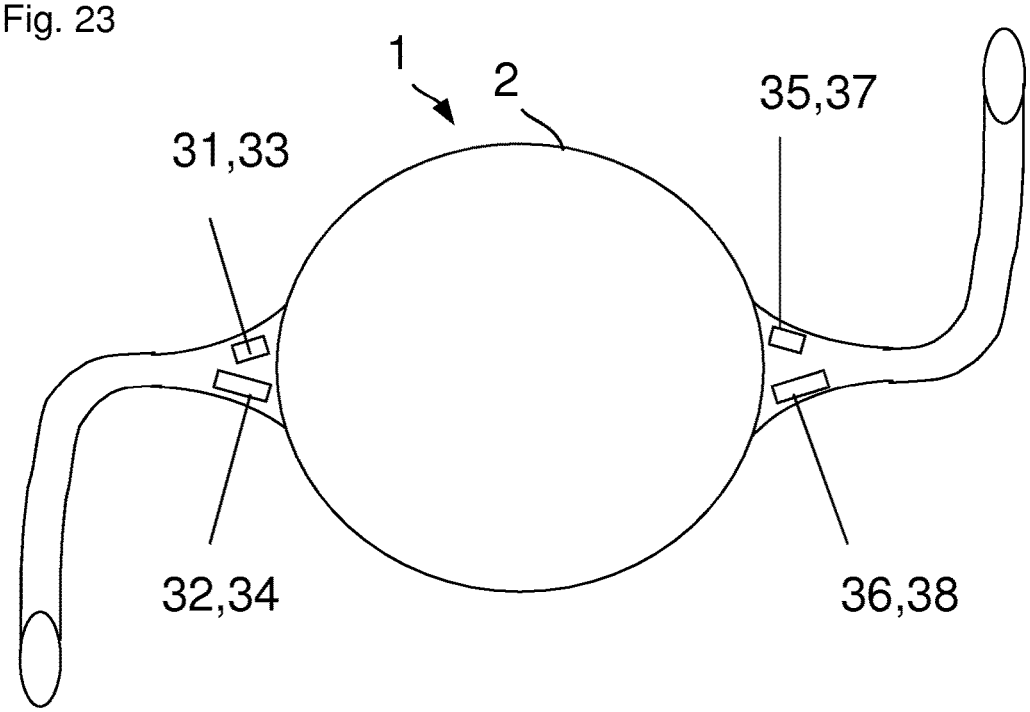
FIG. 23 depicts the intraocular lens of FIG. 19 after specific laser/light irradiation to cause shift of centration in the other lateral direction of the IOL.

As shown in FIG. 23, the main body 2 of the intraocular lens 1 is shifted down relative to the haptic end points by activating zones 32, 34, 36, 38.

Figure 24:
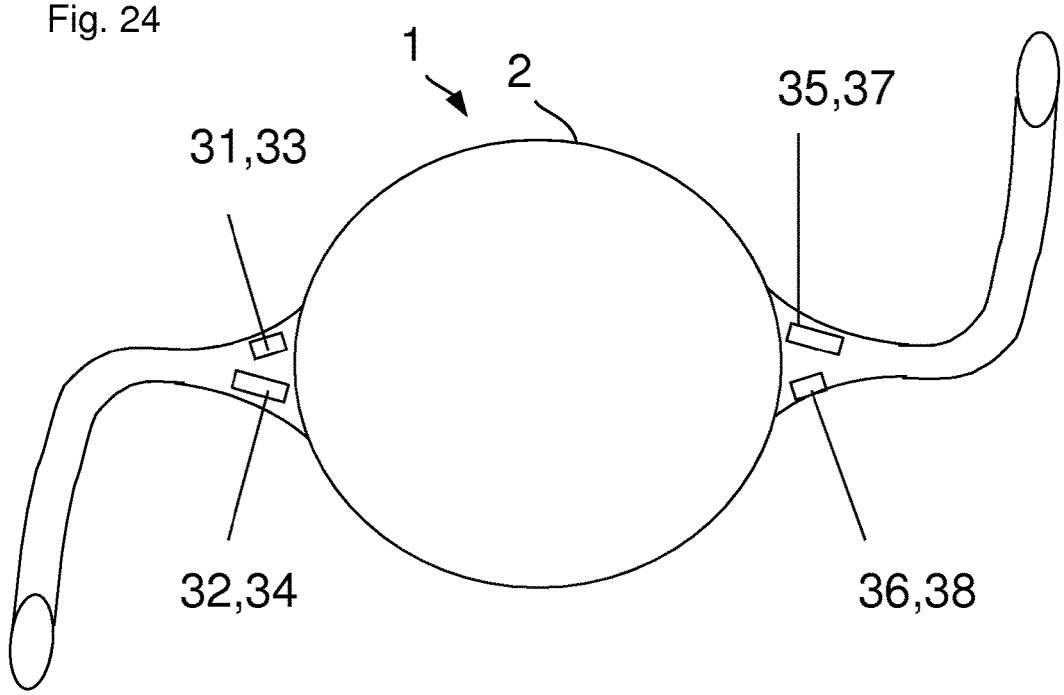
FIG. 24 depicts the intraocular lens of FIG. 19 after specific laser/light irradiation to cause (counter) clockwise rotation of the IOL.

As shown in FIG. 24, the main body 2 of the intraocular lens 1 is rotated counterclockwise relative to the haptic end points by activiating zones 32, 34, 35, 37.

Figure 25:
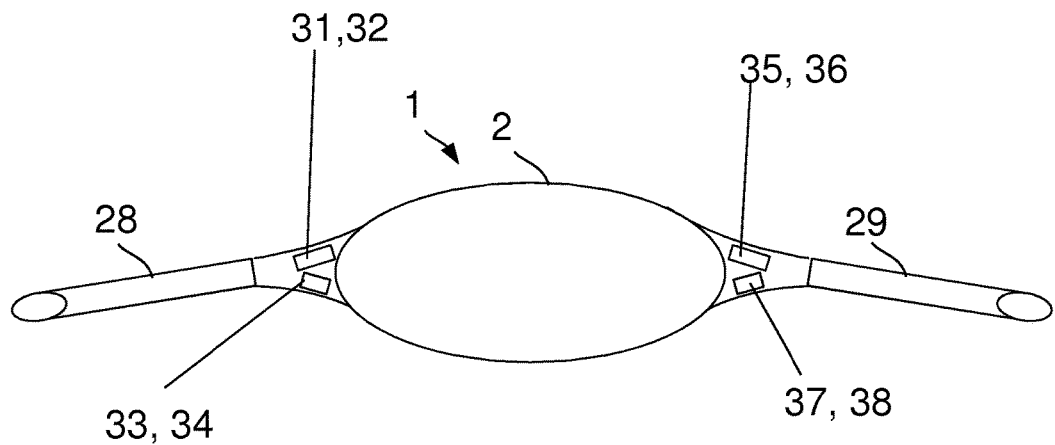
FIG. 25 depicts the intraocular lens of FIG. 19 after specific laser/light irradiation to cause a shift of the IOL along the optical axis.

As shown in FIG. 25, the main body 2 of the intraocular lens 1 is shifted forward/along the optical axis relative to the haptic endpoints by activating zones 31, 32, 35, 36.

Figure 26:
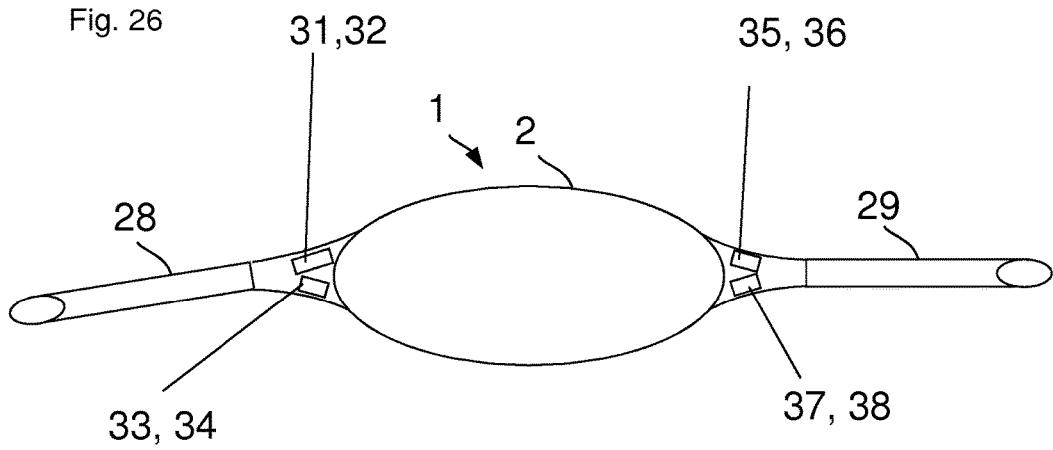
FIG. 26 depicts the intraocular lens of FIG. 19 after specific laser/light irradiation to cause a tilt of the IOL against the optical or visual axis.

As shown in FIG. 26, only the inclination of one of the haptics 28, 29 is changed, leading to a tilt of the intraocular lens 1 relative to the haptic endpoints and thus a tilt to the original optical axis by activating zones 31, 32.

For an expert in the field it is clear that there are other similar embodiments possible.

By mixing the degree of activating of the different zones other movements of the intraocular lens body like tilt along another axis or combination of axial and lateral repositioning and tilt can be realized. In case an activatable zone consists of several separated subzones the degree of activating may be regulated by the number of these subzones being activated.

The activatable zones can be arrange in a different way to realize the necessary change of inclination of the haptic relative to the main body 2 of the intraocular lens 1. In case less degree of freedom is required fewer activatable zones can be realized.

The intraocular lens can be a phakic lens.

The invention claimed is:

1. An intraocular lens for implantation into an eye, comprising:
   a lens body having a central region, haptics for holding the intraocular lens in place within the eye after implantation, and activatable zones located outside the central region;
   wherein the haptics comprise the activatable zones and each haptic comprises a root portion connecting the haptic to the lens body and the activatable zones, the root portions extending outwardly away from the lens body and a remainder of the haptic extending beyond the root portion away from the lens body;
   wherein several of the activatable zones are arranged within the root portion of each haptic;
   wherein the lens body comprises an optical axis;
   wherein, the root portion and the activatable zones are configured such that after implantation of the intraocular lens into the eye at least one of position along the optical axis, rotation and tilt of the central region of the intraocular lens within the eye is changeable upon irradiating only at least some of the activatable zones with laser radiation; and
   wherein at least some of the activatable zones comprise hygroscopic material encapsulated by a hydrophobic layer which can be perforated by the laser radiation.

2. The intraocular lens according to claim 1, wherein at least some of the activatable zones comprise an elastically deformed region which expands at least partly upon being irradiated with the laser radiation.

3. The intraocular lens according to claim 1, wherein at least some of the activatable zones comprise a material having a hygroscopic property, and wherein said hygroscopic property can be enhanced or the material be made to swell or expand by irradiating with laser radiation.

4. The intraocular lens according to claim 1, wherein an internal tension in the material of the lens body and/or the haptics is provided in at least some of the activatable zones.

5. The intraocular lens according to claim 1, wherein the haptics comprise a folded structure.

6. The intraocular lens according to claim 1, wherein at least some of the activatable zones have a ring shape.

7. The intraocular lens according to claim 1, wherein at least some of the activatable zones comprise a plurality of rings.

8. The intraocular lens according to claim 1, wherein the central region has a size at least as large as a dark-adapted pupil of the eye into which it is implanted.

9. The intraocular lens according to claim 1, wherein the activatable zone is rotationally symmetrical in shape.

10. The intraocular lens according to claim 1, wherein the activatable zone is arranged to allow tilting of at least one of the haptics relative to the intraocular lens body.

11. The intraocular lens according to claim 1, wherein, after implantation of the intraocular lens into the eye, at least two of position along the optical axis, rotation and tilt of the intraocular lens change upon irradiating only at least one of the activatable zones with laser radiation.

12. The intraocular lens according to claim 1, wherein at least one of the activatable zones comprises several separated subzones.

13. The intraocular lens according to claim 1, wherein the lens body comprises an activatable zone, wherein, after implantation of the intraocular lens into the eye, the lens body is deformed in the central region upon irradiating only the activatable zone in the lens body with laser radiation.

14. The intraocular lens according to claim 1, wherein at least four activatable zones are arranged in the root portion of one haptic.

15. The intraocular lens according to claim 1, wherein at least one of the activatable zones is arranged in an anterior part of the root portion and at least one of the activatable zones is arranged in a posterior part of the root.

16. In combination, an intraocular lens and a device for changing the optical effect of the intraocular lens, said intraocular lens being implanted into an eye and comprising:
- a lens body having a central region, haptics for holding the intraocular lens in place within the eye after implantation and activatable zones located outside the central region;
- wherein the haptics comprise the activatable zones and each haptic comprises a root portion connecting the haptic to the lens body, the root portions extending outwardly away from the lens body and a remainder of the haptic extending beyond the root portion away from the lens body;
- wherein several of the activatable zones are arranged in the root portion of each haptic,
- wherein the lens body comprises an optical axis; and
    - wherein, the root portion and the activatable zones are configured such that after implantation of the intraocular lens into the eye, at least one of position along the optical axis, rotation and tilt of the central region of the intraocular lens within the eye is changeable upon irradiating only the activatable zones with laser radiation; and
    - wherein at least some of the activatable zones comprise hygroscopic material encapsulated by a hydrophobic layer which can be perforated by the laser radiation; and said device comprising:
- a laser device including a laser radiation source providing laser radiation;
- an optical unit applying said laser radiation to the implanted intraocular lens, and
- a control unit, which controls the laser device such that the laser radiation is directed only in the activatable zones to change at least one of the position along the optical axis, the rotation and the tilt of the intraocular lens.

17. The device according to claim 16, further comprising a measuring unit for measuring an eye-sight defect after implantation of the intraocular lens and providing measuring results, and a generating unit for generating control data depending on the measuring results, wherein operating the changing device with said control data leads to a deformation of the lens body in the central region and/or to a change of at least one of the position, the rotation and the tilt of the intraocular lens within the eye resulting to a reduction of the eye-sight defect.

* * * * *

UNITED STATES PATENT AND TRADEMARK OFFICE
CERTIFICATE OF CORRECTION

PATENT NO. : 10,039,634 B2
APPLICATION NO. : 13/702040
DATED : August 7, 2018
INVENTOR(S) : Manfred Dick et al.

Page 1 of 1

It is certified that error appears in the above-identified patent and that said Letters Patent is hereby corrected as shown below:

In the Specification

Column 2, Line 14, delete "detoriating" and insert --reducing--

Column 3, Line 1, delete "consists" and insert --consist--

Column 3, Line 13, delete "detoriated" and insert --affected--

Column 4, Line 4, delete "generate" and insert --generated--

Column 5, Line 11, after the first occurrence of "step", insert --,--

Column 5, Line 64, delete "shows"

Column 8, Line 4, delete "to" and insert --two--

Column 9, Line 64, delete "same" and insert --some--

Column 10, Line 20, delete "arrange" and insert --arranged--

Signed and Sealed this
Sixth Day of August, 2019

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 10,039,634 B2 | Page 1 of 2 |
| APPLICATION NO. | : 13/702040 | |
| DATED | : August 7, 2018 | |
| INVENTOR(S) | : Manfred Dick et al. | |

It is certified that error appears in the above-identified patent and that said Letters Patent is hereby corrected as shown below:

In the Specification

Column 1, Line 21, delete "a intraocular" and insert --an intraocular--

Column 1, Line 27, delete "form" and insert --from--

Column 1, Line 31, delete "astigmatism" and insert --astigmatism.--

Column 2, Line 9, delete "activable" and insert --activatable--

Column 3, Line 4, delete "hyrdogel" and insert --hydrogel--

Column 3, Line 13, delete "detoriated" and insert --deteriorated--

Column 3, Line 17, delete "plane" and insert --plan--

Column 4, Line 33, delete "defect," and insert --defect, and--

Column 5, Line 39, delete "region" and insert --region,--

Column 5, Line 41, delete "lens," and insert --lens, and--

Column 6, Line 32, delete "b" and insert --21b--

Column 6, Line 32, delete "activable" and insert --activatable--

Column 6, Line 35, delete "b" and insert --22b--

Column 6, Line 46, delete "axis;" and insert --axis; and--

Signed and Sealed this
Twenty-first Day of April, 2020

Andrei Iancu
*Director of the United States Patent and Trademark Office*

CERTIFICATE OF CORRECTION (continued)
U.S. Pat. No. 10,039,634 B2

Column 7, Line 19, delete "deformed" and insert --deformed outer--

Column 8, Line 56, delete "an" and insert --a--

Column 9, Line 6, delete "an" and insert --a--

Column 9, Line 47, delete "a intraocular" and insert --an intraocular--

Column 10, Line 3, delete "activiating" and insert --activating--